US008023592B2

(12) United States Patent
Rose (10) Patent No.: US 8,023,592 B2
(45) Date of Patent: Sep. 20, 2011

(54) METHOD AND APPARATUS FOR FINDING CENTER AMPLITUDE OF PARTICLE SIZE-REPRESENTATIVE PULSES PRODUCED BY APERTURE BASED SIZING SYSTEM

(75) Inventor: Jeffrey L. Rose, Pembroke Pines, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 882 days.

(21) Appl. No.: 11/210,352

(22) Filed: Aug. 24, 2005

(65) Prior Publication Data

US 2007/0047674 A1    Mar. 1, 2007

(51) Int. Cl.
*H04L 27/06* (2006.01)
(52) U.S. Cl. ......... 375/340; 375/316; 375/341; 375/342
(58) Field of Classification Search ................... 375/340
See application file for complete search history.

(56) References Cited

U.S. PATENT DOCUMENTS

| | | | |
|---|---|---|---|
| 3,668,531 A * | 6/1972 | Hogg ............................... | 327/50 |
| 3,710,263 A | 1/1973 | Doty et al. | |
| 3,820,019 A | 6/1974 | Doty et al. | |
| 3,863,159 A * | 1/1975 | Coulter et al. ................... | 327/70 |
| 3,863,160 A * | 1/1975 | Doty ............................... | 327/70 |
| 3,963,983 A | 6/1976 | Hogg | |
| 4,009,443 A | 2/1977 | Coulter et al. | |
| 4,110,604 A | 8/1978 | Haynes et al. | |
| 4,797,624 A | 1/1989 | Dunstan et al. | |
| 4,935,950 A * | 6/1990 | Ranallo et al. ................. | 378/207 |
| 5,133,602 A | 7/1992 | Batchelder et al. | |
| 5,561,515 A * | 10/1996 | Hairston et al. ................. | 356/28 |
| 5,805,460 A * | 9/1998 | Greene et al. .................... | 702/79 |
| 6,196,973 B1 * | 3/2001 | Lazenby et al. ............... | 600/458 |
| 6,282,218 B1 * | 8/2001 | Anderson ................... | 372/38.02 |
| 6,624,798 B1 * | 9/2003 | Aoki et al. ....................... | 345/60 |
| 2002/0061080 A1 * | 5/2002 | Richards et al. .............. | 375/346 |
| 2005/0017707 A1 * | 1/2005 | Ramesh et al. ............... | 324/102 |
| 2006/0222132 A1 * | 10/2006 | Beaudoin et al. ............. | 375/360 |

* cited by examiner

*Primary Examiner* — Shuwang Liu
*Assistant Examiner* — Michael Neff
(74) *Attorney, Agent, or Firm* — Sterne, Kessler, Goldstein & Fox P.L.L.C.

(57) ABSTRACT

Pipelined digital processing circuitry for use with a particle size measurement system, such as that employed in automated hematology systems, measures the 'center' amplitude of a pulse produced by a particle or cell passing through a flow cell measurement aperture, such as the detection aperture of a Coulter Principle-based electronic particle analysis system. The circuitry of the invention processes successive pulse samples by means of a half-peak/half-width methodology that analyzes each pulse as its continuously sampled and temporarily stored in memory. Concurrent analysis of the data in memory during storage locates the pulse width at a prescribed percentage (e.g., 50%) of the peak amplitude of the pulse. This pulse width data is then processed to determine the pulse amplitude at the midpoint of the width of the pulse between its mid-peak values on rising edge and fall edge portions of the pulse.

10 Claims, 3 Drawing Sheets

METHOD AND APPARATUS FOR FINDING CENTER AMPLITUDE OF PARTICLE SIZE-REPRESENTATIVE PULSES PRODUCED BY APERTURE BASED SIZING SYSTEM

FIELD OF THE INVENTION

The present invention relates in general to particle size measurement systems, such as those employed in automated hematology systems, and is particularly directed to a new and improved digital processing based method and apparatus for measuring the 'center' amplitude of a pulse produced by a particle or cell passing through a flow cell measurement aperture, such as the detection aperture of a Coulter Principle-based electronic particle analysis system.

BACKGROUND OF THE INVENTION

Figure 1:
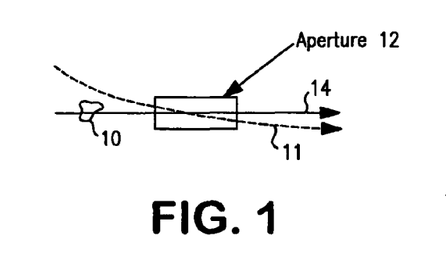
FIG. 1 diagrammatically illustrates axial and non-axial trajectories of particles passing through a detection aperture.
Figure 2:
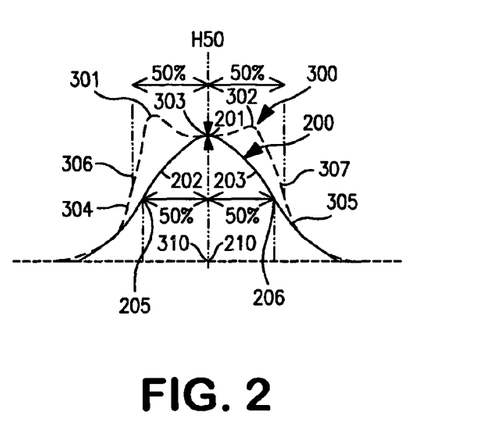
FIG. 2 shows examples of shapes of pulses produced by particles passing along the axial and non-axial trajectories through the detection aperture shown in FIG. 1.

Most blood analyzer systems in use today measure microscopic particles/cells in a blood sample by means of electrically and/or optically based measurements. In a Coulter/impedance-based electrical measurement system, particles within a carrier fluid passing through a detection aperture cause the generation of electrical pulses proportional to their volume; using some form of thresholding technique on the pulses, the particles that give rise to the pulses may be classified as platelets, erythrocytes (red blood cells (RBCs)), or leukocytes (white blood cells). As shown in FIG. 1, in an ideal case, the trajectory of a particle 10 passing through the detection aperture 12 will be coincident with its central axis 14, so as to produce a pulse as shown at 200 in FIG. 2, the pulse having a central peak 201 that is bounded by a pair of relatively symmetrically rising and falling sloped portions 202 and 203. In the real world, however, many pulses travel through the detection aperture along non-axial trajectories, as shown at 11 in FIG. 1. Because the electrical field strength is non-uniform throughout the aperture, a particle passing near an edge of the aperture will typically give rise to what is classically referred to as an 'M' shaped pulse, shown at 300 as having a pair of peaks, as shown at 301 and 302 in FIG. 2 on either side of the center 303 of the pulse. Thus, the peak value for identical particles will vary depending upon the path of the particles through the aperture.

One very successful prior art technique developed by the assignee of the present application, and described in the U.S. patent to Doty et al, U.S. Pat. No. 3,710,263, involves an editing technique that discards undesirable pulses based upon their width at 50% and 75% of the peak. Editing, however, has the disadvantage that it loses a captured event, thereby requiring more time to build up an accurate histogram of the particle size distribution. In addition, this technique applies the same pulse width limits on all pulse heights, potentially over-editing some populations and under-editing others. An alternate sizing scheme, using the pulse amplitude at the time the particle is halfway through the aperture, has long been considered a superior technique for more accuracy without editing, yielding an accurate result more quickly with fewer pulses. The U.S. patent to Doty, U.S. Pat. No. 3,863,160, describes an analog system for accomplishing this approach. This analog system uses integration and delay lines to find a mid-flight point which, unfortunately, is inaccurate on asymmetric pulses, has limited throughput due to fixed delays and circuit state overhead, and is difficult to construct due to tolerance stack-up.

SUMMARY OF THE INVENTION

In accordance with the present invention, drawbacks of conventional particle size measurement schemes, such as those described above, are effectively obviated by digitizing the pulses produced by the aperture measurement circuitry and processing the digitized pulses through pipelined digital processing circuitry. To this end, the pulse is continuously sampled and temporarily stored in memory. Concurrent analysis of the data in memory during storage locates the pulse width at a prescribed percentage (e.g., 50%) of the peak amplitude of the pulse. This pulse width data is then processed (e.g., divided in half) to determine the pulse amplitude at a prescribed percentage the midpoint of the width of the pulse.

For this purpose, the digital processing circuitry of the present invention includes logic circuitry that is operative to capture the peak value of the pulse and to drive a counter, in sampling clock cycles for the duration of the pulse being analyzed. An analog-to-digital (A-D) converter installed at the front end of the system is continuously sampling the output of the flow cell's aperture monitoring circuitry. The output of the A-D converter constitutes the sampled data which is examined for the presence of a pulse produced by a particle passing through the detection aperture. For this purpose, a prescribed pulse detection threshold associated with a minimum value of what will be accepted as a valid pulse (namely some value above an established Pulse Above Noise (PAN) floor) is coupled to a first input of a pulse threshold comparator. The pulse threshold comparator has a second input coupled to receive the digital value of each sample of the output of the aperture monitoring sensor. As long as the value of the sampled data does not exceed the pulse detection threshold (indicating that a particle is not present in the flow cell aperture), the output of the comparator is at a first logical state. This causes a peak value storage register to be cleared and, via an inverter asserting a '0' or low at the enable input of a pulse duration counter and also clearing the contents of counter by asserting a '1' at its clear input. As described below, the contents of the pulse duration counter define a write address for storing the sampled data value in random access memory (RAM).

Eventually, as a particle enters the flow cell aperture, the output of the aperture monitoring sensor will increase to a (Pulse Above Noise or PAN) value above the pulse detection threshold supplied to the pulse threshold comparator. When this happens, the sampled data input value input of the pulse threshold comparator will exceed the threshold value, and the output of the comparator will change state. This serves to remove the '1' previously applied to the clear input of the peak value storage register and to the clear input of the pulse duration counter. Namely, the pulse above noise (PAN) output of the inverter is now asserted high, and PAN-NOT is asserted low. As a consequence, a logical '1' is applied to the enable input of the pulse duration counter, so that the counter may begin to count clock pulses associated with the sampling of the data and applied at the counter's clock input.

With the PAN-NOT value changing from a logical '1' to a logical '0', there is no longer a continuous clear being asserted to the CLR input of the peak value storage counter. The current contents of the peak value storage register, which are all zeros since the register has been continuously cleared, are applied to the peak comparator wherein they are compared with the value of the sampled data which currently exceeds the pulse detection threshold, applied to the comparator. Since the value of the sampled data exceeds the value of the previously cleared contents of the peak value storage register, then output of the peak comparator changes state thereby asserting a '1' at the enable input of the peak value storage register. As a result, the sampled data value, which is applied to the peak value storage register, will be clocked into that register by the sampling clock signal applied to its clock input. This clock signal is also applied to the clock input of the pulse duration counter, so that the previously cleared contents of the pulse duration counter are incremented to an address representative value of the next sequential address (address location 1).

Thereafter, as the next value of the sampled data is applied to the peak comparator, that value is compared with the initial value of sampled data that was just loaded into the peak value storage register. If the next value of sampled data exceeds that currently stored in the register (and it can be expected to do so for successive sampled locations along the rising slope of the pulse, it will exceed both the pulse detection threshold applied to the pulse threshold comparator and also exceed the sampled value currently stored in peak value storage register) the new value of the sampled data will be written into the peak value storage register in place of the previous value, and the pulse duration counter will be incremented again by the clock signal.

The sequence of events is repeated for each data sample throughout the duration of the pulse, i.e., as long as the value of the pulse remains above the pulse detection threshold. During this process, whether or not a newly sampled data value will be substituted for the value currently residing in the peak value storage register will depend upon whether or not the newly sampled data value exceeds the contents of that register. Once the actual peak value of the pulse has been latched into the peak value storage register, there can expected to be additional pulse data sample values for the remainder of the pulse; however, these values will not written into the peak value storage register, since they are less than the value within that register which is applied to the peak comparator. Eventually (at the termination of the pulse), the sampled data value applied to the pulse threshold comparator will no longer exceed the pulse detection threshold value, at which time further incrementing of the pulse duration counter is terminated by the change in state of the PAN signal applied to its enable input. In response to the termination of the pulse, the change in state of the output of the pulse threshold comparator is used to transfer the contents of peak value storage register and pulse duration counter to an associated set of parallel registers for use in subsequent signal processing.

The control logic of the invention further includes digital processing circuitry used to store the successive samples of a pulse and to identify the location on the rising edge of the pulse that corresponds to half the peak amplitude value. For this purpose, the contents of the peak value storage register are coupled to a first input of a multiplier to a second input of which, a prescribed fraction (0.5 in the present example) is applied. As a non-limiting example, for the particular case of 0.5, the contents of the register containing the digital value stored in peak value storage register may be simply right-shifted by one bit, and applied to a one-half peak comparator 70. The one-half peak comparator is coupled to receive the value of a data sample stored in that location or address in a RAM pointed to by the digital code supplied to a read address input thereof. As data samples of the pulse of interest are supplied to the peak comparator 50 described above, they are successively written into RAM at successive addresses defined in accordance with the contents of the pulse duration counter. For this purpose, the sampled data is coupled to the RAM's data input port, while the contents of the pulse duration counter are coupled to the RAM's write address port. The sampling clock is coupled to the RAM's clock input port, functioning as the write strobe.

Initially, sampled data values are read out of memory in accordance with the contents of a read address counter, which is sequentially clocked by the read clock applied to its clock input. When enabled by the output of the one-half peak comparator applying a logical '1' to its enable input, the contents of a read address counter (initially cleared by the PAN-NOT output being asserted high '1') are sequentially incremented. The digital code value of these contents is coupled via a multiplexer to the read address port of the RAM. The multiplexer initially has its output port coupled to receive the ½ peak rising address by the PAN-NOT signal having been asserted at the select port of the multiplexer. As a consequence, the contents of read address counter serve as the read address for the RAM. As described above, the PAN-NOT signal is de-asserted for the duration of a pulse. Once processing of a pulse has been completed, the PAN_NOT signal is again asserted high (logical '1'), at which time the address of the value of the pulse at a location on the pulse midway between those locations on the rising and falling portions of the pulse that have values equal to half the amplitude of the peak value of the pulse is coupled through the multiplexer to the read address port of the RAM.

This logic circuitry operates as follows. With the read address counter cleared by the PAN-NOT signal, its contents will initially be all zeroes, so as to point to the address in RAM into which the first valid data sample has been written. The value of data sample at that address is coupled to the one-half peak comparator to be compared with ½ the pulse peak value currently stored in the peak value storage register. When the value of half the peak code currently stored in the peak value storage register is greater than the value of data sample being pointed to by the contents of read address counter, that counter is enabled and incremented by the read clock supplied to its clock port. However, once the value of half the peak code currently stored in the peak value register does not exceed the value of the data sample being pointed to by the contents of the counter, the counter is disabled and thereby prevented from incrementing. This has the effect of causing the read address counter to be repeatedly incremented, as it temporarily pauses and then resumes incrementing as the contents of the peak value storage register are sequentially increased towards the peak value of the pulse. This has the effect of causing the logic circuitry to walk up the rising edge of the pulse. Once the peak value of the pulse has been written into the peak value storage register, no further incrementing of the contents of that register will take place. The count value within the read address counter will, after iteration, contain that address in RAM containing the first pulse sample value equal to or greater than one-half the peak value of the pulse. This address is identified as the ½ peak rising address, and is supplied to further logic for the purpose of determining the width of the pulse between those samples on the rising and falling edges of the pulse whose amplitude values equal or have just passed one-half the peak value. As a portion of the logic is locating the ½ peak rising address, a companion portion of the logic operates to locate the ½ peak falling address.

For this purpose, sampled data is clocked into a single clock delay register and is further supplied to a ½ peak greater than sample comparator. The ½ peak register value is coupled to the comparator and to a delayed sample greater than or equal to ½ peak comparator. The delayed data sample is also coupled to the comparator. The outputs of these two comparators are coupled to an AND gate, the output of which is coupled to the enable (EN) input of a ½ peak register. The D input of the ½ peak register is coupled to receive the pulse duration address, while its Q output is coupled to provide the address of the ½ falling peak. The ½ falling peak register is clocked by a clock signal applied to its clock port. The ½ falling peak logic operates as follows. As successive data samples are applied to the single clock delay, they are delayed by one clock cycle and then applied to the ½ peak comparator with the value of the ½ peak supplied to the comparator. At the same time the undelayed data is compared in ½ peak greater than sample comparator. When the single clock delayed data sample is greater than or equal to the ½ peak value, so that the output of the comparator is high or a '1', and the non-delayed data sample is less than or equal to the 1/2 peak value, so that the output of the other comparator is high or a '1', the output of AND gate is high or a '1'. The output of AND gate going high indicates that the location of the ½ peak on the falling edge of the pulse has been bracketed by the two comparators. The AND gate thereby supplies an enabling input to the register, so that the pulse duration count which currently points to the location of the ½ peak value one the falling edge of the pulse may be captured as the address in the RAM pointing to that falling edge ½ peak location. This address is coupled from the output of the register to midpoint width and height determining logic.

More particularly, the falling edge ½ peak address value is coupled to a first, minuend (+) input of a subtraction unit which has a second, subtrahend (−) input coupled to receive the rising edge ½ peak address supplied by the counter. At its output the subtraction unit produces an address code "t50" corresponding to the difference between the address of the falling edge ½ peak address value and the address of the rising edge ½ peak address value. By dividing this address code difference in half, the system will locate the middle of the pulse halfway between its two midpeak values on its rising and falling edges. To this end, the output of the subtraction unit is coupled to a multiplier which multiplies the difference address value by 0.5 (as noted above this may be readily accomplished by a right shift of the address difference code). The output of the multiplier is an address differential from the address of the ½ peak pulse value on the rising edge of the pulse to the value of the pulse located midway between the two midpeak values on its rising and falling edges. In order to derive the actual address of the value of the pulse at this midway address location, it is necessary to add the address differential produced by the 0.5 multiplier to the rising edge ½ peak address value supplied to the subtraction unit. For this purpose, the output of the multiplier is coupled to a first summing input of an adder while the address code for the rising edge ½ peak address is supplied to the second summing input of the adder. The output of the adder is therefore the actual address of the value of the pulse located midway between its ½ peak rising edge value and its ½ peak falling edge value. The address is termed the "H50" address as it points to the address of the height (H) of the pulse at 50% of its width between the ½ peak values on its rising and falling edges. The H50 address is coupled to the multiplexer so that its may be loaded into memory when PAN-NOT is asserted as a '1'.

The pulse width in clocks termed as a t50 value, as produced by the subtraction unit, and the pulse height H50 at the pulse midpoint provided by the RAM are coupled to downstream processing circuitry for further processing and analysis of the pulse data. It may be noted that the pulse height value H50 is readily derived in a single sampling clock cycle following the end of a pulse, so that there is no dead time in the acquisition. Distinct pulses, by definition, have at least one clock cycle between the detection threshold between them. Noise pulse, or glitches, are handled on-the-fly and do not affect analysis of subsequent pulses, regardless of proximity in time.

DETAILED DESCRIPTION

Before detailing the methodology and architecture for measuring the 'center' amplitude of a pulse produced by a particle passing through a flow cell measurement aperture in accordance with the present invention, it should be observed that the invention resides primarily in a prescribed novel arrangement of conventional digital processing circuits and components. Consequently, the configurations of such circuits and components have been shown in the drawings by readily understandable logic and associated waveform diagrams, which show only those specific aspects that are pertinent to the present invention, so as not to obscure the disclosure with details which will be readily apparent to those skilled in the art having the benefit of the description herein. Thus, the digital processing logic diagrams are primarily intended to show the major components of the invention in convenient functional groupings, whereby the present invention may be more readily understood.

Figure 3:
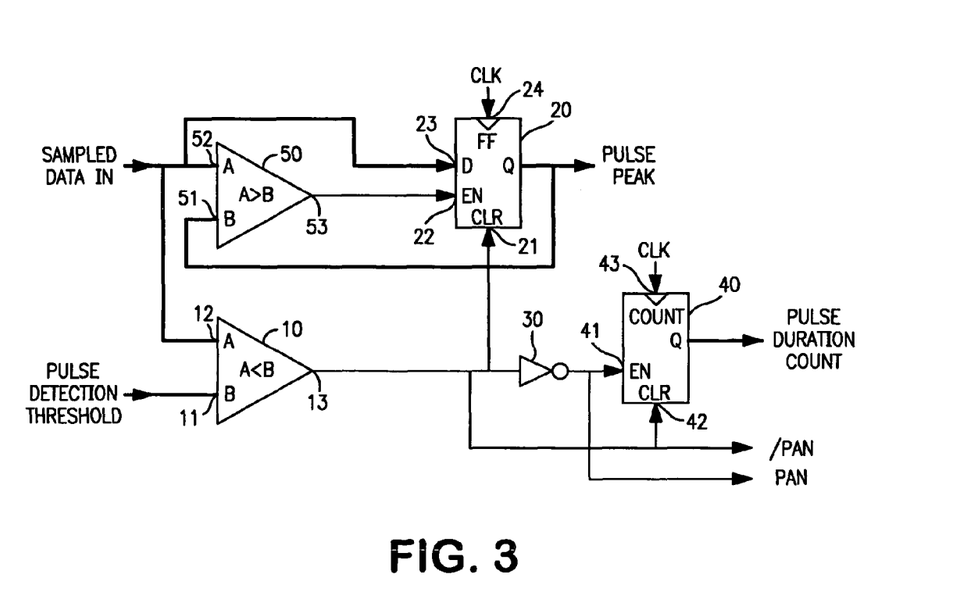
FIG. 3 is a logic diagram of circuitry employed to capture the peak value of a particle-representative pulse and to drive a counter in sampling clock cycles for the duration of the pulse produced by a particle in a flow cell aperture in accordance with the present invention.

Attention is initially directed to FIG. 3, which is a logic diagram of circuitry employed to capture the peak value of the pulse and to drive a counter in sampling clock cycles for the duration of the pulse being analyzed. An analog-to-digital (A-D) converter (not shown) installed at the front end of the system is continuously sampling the output of the flow cell's aperture monitoring circuitry. The output of the A-D converter constitutes the sampled data which is examined by the circuitry of FIG. 3 for the presence of a pulse produced by a particle passing through the detection aperture. For this purpose, a prescribed pulse detection threshold associated with a minimum value of what will be accepted as a valid pulse (namely some value above an established noise floor) is coupled to a first (B) input 11 of a pulse threshold comparator 10. Pulse threshold comparator 10 has a second (A) input 12 coupled to receive the digital value of each sample of the output of the aperture monitoring sensor. As long as the value of the sampled data (A) does not exceed the pulse detection threshold (B), which indicates that a particle is not present in the flow cell aperture, the output 13 of comparator 10 is at a first logical state (e.g., a high or '1'), causing a peak value storage register 20 to be cleared at its clear (CLR) input 21 and, via an inverter 30, asserting a '0' or low at the enable (EN) input 41 of a pulse duration counter 40, and also clearing the contents of counter 40 by asserting a '1' at the clear (CLR) input 42 of pulse duration counter 40. As will be described below with reference to FIG. 4, the contents of the pulse duration counter 40 define a write address for storing the sampled data value in random access memory (RAM).

Eventually, however, as a particle enters the flow cell aperture, the output of the aperture monitoring sensor will increase to a value above the pulse detection threshold (B) supplied to input 11 of the pulse threshold comparator 10. When this happens, the sampled data input value (A) input 12 of pulse threshold comparator 10 will exceed the threshold value (B) supplied to input 11, and the output 13 of comparator 10 will change state (go low to a '0' logic level). This serves to remove the '1' previously applied to the clear input 21 of peak value storage register 20 and to the clear input 42 of pulse duration counter 40. Namely, the pulse above noise (PAN) output of inverter 30 is now asserted high, and PAN-NOT is asserted low. As a consequence, a logical '1' is applied to the enable (EN) input 41 of the pulse duration counter 40, so that counter 40 may begin to count clock pulses associated with the sampling of the data and applied at the counter's clock input 43.

With the PAN-NOT value changing from a logical '1' to a logical '0', there is no longer a continuous clear being asserted to the CLR input 21 of peak value storage counter 20. The current contents of register 20, which are all zeros (since register 20 has been continuously cleared), are applied to the (B) input 51 of peak comparator 50, wherein they are compared with the value of the sampled data which currently exceeds the pulse detection threshold, applied to the (A) input 52 of comparator 50. Since the value of the sampled data (A) exceeds the value (B) of the previously cleared contents of register 20, then within peak comparator 50 the relationship A>B is satisfied and the output 53 of peak comparator 50 changes stage (goes high to a logical '1'), thereby asserting a '1' at the enable (EN) input 22 of peak value storage register 20. As a result, the sampled data value, which is applied to the D input 23 of register 20, will be clocked into register 20 by the sampling clock signal applied to its clock input 24. This clock signal is also applied to the clock input 43, so that the previously cleared contents of pulse duration counter 40 are incremented to a value of 1.

Thereafter, as the next value of the sampled data is applied to the (A) input 52 of peak comparator 50, it is compared with the initial value of sampled data that was just loaded into the register 20. If the next value of sampled data exceeds that currently stored in the register 20 (and it can be expected to do so for successive sampled locations along the rising slope of the pulse, such as along the rising edge 202 of pulse 200 or the rising edge 304 of the pulse 300 shown in FIG. 2), it will exceed both the pulse detection threshold applied to the (B) input 11 of pulse threshold comparator 10 and also exceed the sampled value currently stored in peak value storage register 20. As a result, the new value of the sampled data will be written into the register 20 in place of the previous value, and the pulse duration counter 40 will be incremented again by the clock signal applied to clock input 43.

The above-described routine is repeated for each data sample throughout the duration of the pulse, i.e., as long as the value of the pulse remains above the pulse duration threshold. During this process, whether or not a newly sampled data value will be substituted for the value currently residing in the peak value storage register 20 will depend upon whether or not the newly sampled data value exceeds the contents of that register (such as peak value 201 for pulse 200 and peak value 301 for pulse 300 in FIG. 2). Once the actual peak value of the pulse has been latched into register 20, there can expected to be additional pulse data sample values for the remainder of the pulse; however, these values will not written into the peak value storage register 20, since they are less than the value within that register which is applied to the (B) input 51 of peak comparator 50. Eventually (at the termination of the pulse), the sampled data value applied to the A input 12 of pulse threshold comparator 10 will no longer exceed the pulse detection threshold value applied to its B input 11, at which time further incrementing of the pulse duration counter 40 is terminated by the change in state of the PAN signal applied to its enable input 41. In response to the termination of the pulse, the change in state of the output 13 of pulse threshold comparator 10 is used to transfer the contents of register 20 and counter 40 to an associated set of parallel registers for use in subsequent signal processing, to be described.

Figure 4:
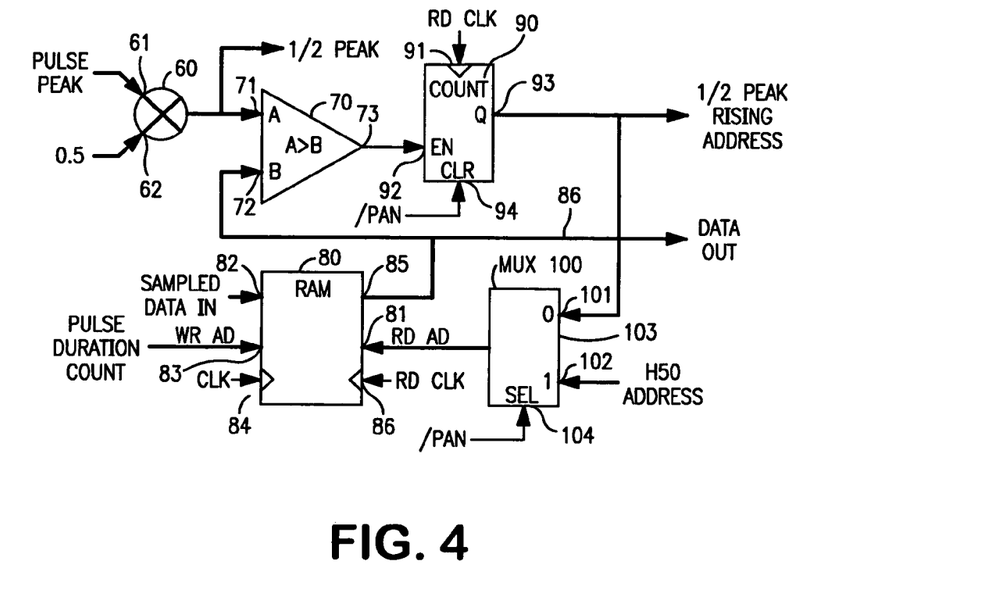
FIG. 4 is a logic diagram of that portion of the digital processing circuitry of the present invention used to store the successive samples of a pulse and to identify the location on the rising edge of the pulse that corresponds to half the peak amplitude value.

FIG. 4 is a logic diagram of that portion of the digital processing circuitry of the present invention used to store the successive samples of a pulse and to identify the location on the rising edge of the pulse that corresponds to half the peak amplitude value. For the pulses shown in FIG. 2 this would correspond to a pulse value along rising edge 202 equal to half the height of the peak 201 for the generally symmetric pulse 200, and a pulse value along the rising edge 304 equal to half the height of the peak 310 for the generally M-shaped pulse 300. For this purpose, the contents of the peak value storage register 20 (FIG. 3) are coupled to a first input 61 of a multiplier 60, to a second input 62 of which, a prescribed fraction (0.5 in the present example) is applied. As a non-limiting example, for the particular case of 0.5, the contents of the register containing the digital value stored in peak value storage register may be simply right-shifted by one bit, and applied to the (A) input 71 of one-half peak comparator 70. The second (B) input 72 of one-half peak comparator 70 is coupled to receive the value of a data sample stored in that location or address in a RAM 80 pointed to by the digital code supplied to a read address input 81.

As noted above, as data samples of the pulse of interest are supplied to the comparator circuitry of FIG. 3, they are successively written into RAM 80 at successive addresses defined in accordance with the contents of the pulse duration counter 40. For this purpose, the sampled data is coupled to the RAM's data input port 82, while the contents of the pulse duration counter 40 are coupled to write address port 83. The sampling clock is coupled to the RAM's clock input port 84. As data is read out of the RAM 80 by a read clock applied to read clock port 81, it asserted from a data output port 85 onto a system data bus 86. Initially, sampled data values are read out of memory in accordance with the contents of a read address counter 90, which is sequentially clocked by the read clock applied to its clock input 91. Counter 90 is cleared by the PAN-NOT signal applied to its clear port 94. When enabled by the output 73 of the one-half peak comparator 70 applying a logical '1' to the enable (EN) input 92, the contents of read address counter 90 (initially cleared by the PAN-NOT output of the logic of FIG. 3 being asserted high '1') are sequentially incremented. The digital code value of these contents are coupled via a multiplexer 100 to the read address port 81 of RAM 80. Multiplexer 100 initially has its output port 103 coupled to its input port 101 by the PAN-NOT signal having been asserted at the selected (SEL) port 104 of the multiplexer. As a consequence, the contents of read address counter 90 serve as the read address for the RAM 80. As described above, the PAN-NOT signal is de-asserted for the duration of a pulse. Once processing of a pulse has been completed, the PAN_NOT signal is again asserted high (logical '1'), at which time the address of the value of the pulse at a location on the pulse midway between those locations on the rising and falling portions of the pulse that have values equal to half the amplitude of the peak value of the pulse is coupled through multiplexer 100 to the read address port 81 of the RAM 80.

The logic of FIG. 4 operates as follows. With read address counter 90 cleared by the PAN-NOT signal, its contents will initially be all zeroes, so as to point to the address in RAM 80 into which the first valid data sample has been written. The value of data sample at that address is coupled to the B input 72 of the one-half peak comparator 70 to be compared with ½ the pulse peak value currently stored in peak value storage register 20 (FIG. 3). Unless the value of half the peak code currently stored in register 20 is greater than the value of data sample being pointed to by the contents of read address counter 90, counter 90 is disabled and thereby prevented from incrementing. However, once the value of half the peak code currently stored in register 20 exceeds the value of data sample being pointed to by the contents of counter 90, counter 90 is enabled and thereby incremented by the read clock supplied to its clock port 91. This has the effect of causing the read address counter 90 to be repeatedly incremented, as it temporarily pauses and then resumes incrementing as the contents of the peak value storage register 20 are sequentially increased towards the peak value of the pulse. This has the effect of causing the circuitry of FIG. 4 to walk up the rising edge of the pulse, such as rising edge 202 for pulse 200 and the rising edge 304 for the pulse 300 in FIG. 2. Once the peak value of the pulse has been written into register 20, no further of the contents of register 20 will take place, as described above. The count value within read address counter 90 will, after iteration, then contain that address in RAM 80 containing the first pulse sample value equal to or greater than one-half the peak value of the pulse. In the pulse diagram of FIG. 2, this corresponds to the ½ peak point 205 on rising edge 202 of pulse 200, and the ½ peak point 306 on the rising edge 304 of the M-shaped pulse 300. This address is identified in FIG. 4 as the ½ peak rising address, and is supplied to the logic shown in FIG. 6 for the purpose of determining the width of the pulse between those portions on the rising and falling edges of the pulse whose amplitude values equal one-half the peak value, as will be described. As the logic of FIG. 4 is locating the ½ peak rising address, companion logic in FIG. 5 operates to locate the ½ peak falling address.

For this purpose, sampled data is clocked into a single clock delay register 110 and is further supplied to the (B) input port 121 of a ½ peak greater than sample comparator 120. The ½ peak value from multiplier 60 is coupled to the second (A) input 122 of comparator 120 and to a first (B) input 131 of delayed sample greater than or equal to ½ peak comparator 130. The delayed data sample is coupled to a second (A) input 132 of comparator 130. The outputs of comparators 120 and 130 are coupled to AND gate 140, the output of which is coupled to the enable (EN) input 151 of a ½ peak register 150. The D input 152 of register 150 is coupled to receive the pulse duration address, while its Q output 153 is coupled to provide the address of the ½ falling peak. The ½ falling peak register 150 is clocked by a clock signal applied to its clock port 154. The ½ falling peak logic of FIG. 5 operates as follows. As successive data samples are applied to delay 110, they are delayed by one clock cycle and then applied to the ½ peak comparator 130 with the value of the ½ peak supplied to the (B) input 131 in comparator 130. At the same time the undelayed data is compared in ½ peak greater than sample comparator 120. When the single clock delayed data sample is greater than or equal to the ½ peak value, so that the output of comparator 130 is high or a '1', and the non-delayed data sample is less than the ½ peak value, so that the output of comparator 120 is high or a '1', the output of AND gate 140 is high or a '1'. The output of AND gate going high indicates that the location of the ½ peak on the falling edge of the pulse has been bracketed by the two comparators. AND gate 140 thereby supplies an enabling input to register 150, so that the pulse duration count which currently points to the location of the ½ peak value on the falling edge of the pulse may be captured as the address in the RAM pointing to that falling edge ½ peak location. In the pulse diagram of FIG. 2, this corresponds to the ½ peak location 206 on the falling edge 203 of the pulse, and the ½ peak location 307 on the falling edge 305 of M-shaped pulse 300. This address is coupled from the output 153 of register 150 to midpoint width and height determining logic in FIG. 6.

Figure 5:
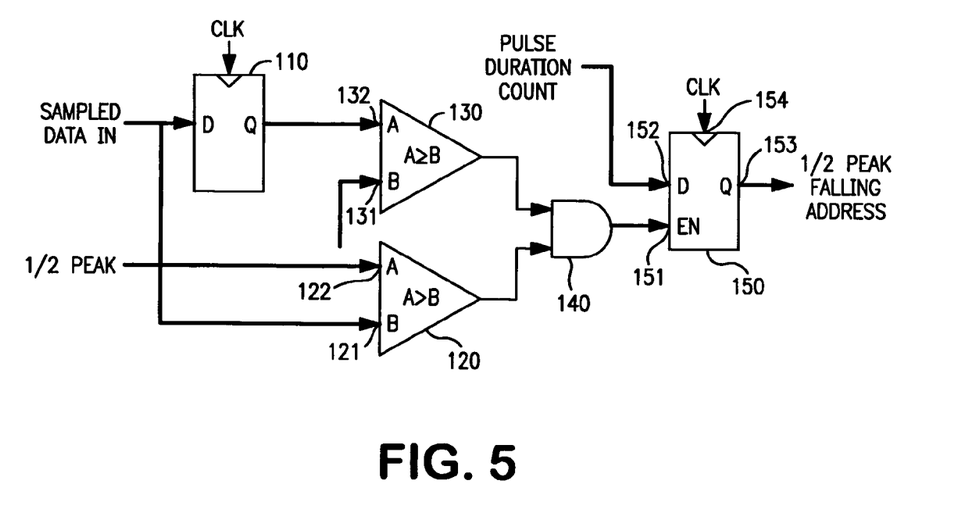
FIG. 5 is companion logic to the logic of FIG. 4 and is operative to locate the ½ peak falling address.
Figure 6:
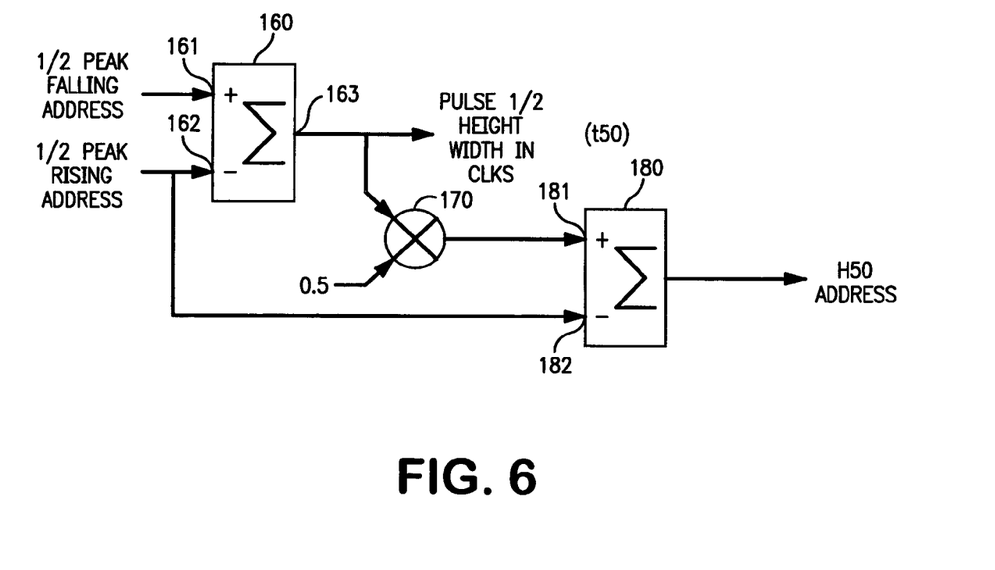
FIG. 6 is logic that is operative to determine the width of the pulse between those portions on the rising and falling edges of the pulse whose amplitude values equal one-half the peak value and calculate the address of the H50 value in memory.

More particularly, as shown in FIG. 6 the falling edge ½ peak address value produced by register 150 in FIG. 5 is coupled to a first, minuend (+) input 161 of a subtraction unit 160, which has a second, subtrahend (−) input 162 coupled to receive the rising edge ½ peak address supplied by counter 90 (FIG. 4). At its output 163, subtraction unit 160 produces an address code, labeled as t50 and corresponding to the difference between the address of the falling edge ½ peak address value and the address of the rising edge ½ peak address value. By dividing this address code difference in half, and adding it to the ½ peak address code, the system will locate the middle of the pulse halfway between its two midpeak values on its rising and falling edges. To this end, the output 163 of subtraction unit 160 is coupled to a multiplier 170 which multiplies the difference address value by 0.5 (as noted above this may be readily accomplished by a right shift of the address difference code). The output of multiplier 170 is an address differential from the address of the ½ peak pulse value on the rising edge of the pulse to the value of the pulse located midway between the two midpeak values on its rising and falling edges. In order to derive the actual address of the value of the pulse at this midway address location, it is necessary to add the address differential produced by multiplier 170 to the address of the ½ peak address supplied to input 162 of subtraction unit 160. For this purpose, the output of multiplier 170 is coupled to a first summing input 181 of adder 180, while address code for the ½ peak address supplied to input 162 of subtraction unit 160 is supplied to the second summing input 182 of adder 180. The output of adder 180 is therefore the actual address of the value of the pulse located midway between its ½ peak rising edge value and its ½ peak falling edge value. In the pulse diagram of FIG. 2, this resulting address corresponds to the midpulse location 210 for pulse 200 and midpulse location 310 for pulse 300. The address is termed the H50 address as it points to the address of the height (H) of the pulse at 50% of its width between the ½ peak values on its rising and falling edges. The H50 address is coupled to input port 102 of multiplexer 100, so that its may be loaded into memory 80 when PAN-NOT is asserted as a '1'.

The pulse width in clocks termed as a t50 value, as produced by the output 163 of subtraction unit 160, and the pulse height H50 at the pulse midpoint provided by RAM 80 are coupled to downstream processing circuitry for further processing and analysis of the pulse data. It may be noted that the peak pulse value H50 is readily derived in a single sampling clock cycle following the end of a pulse, so that there is no dead time in the acquisition. Distinct pulses, by definition, have at least one clock cycle below the detection threshold between them. Noise pulses, or glitches, are handled on-the-fly and do not affect analysis of subsequent pulses, regardless of proximity in time.

As will be appreciated from the foregoing description, the pipeline digital processing circuitry in accordance with the particle size measurement system of the present invention successfully remedies drawbacks of conventional particle size measurement schemes, such as those described above, by digitizing the pulses produced by the aperture measurement circuitry and then processing by means of a half-peak/half-width methodology that analyzes each pulse as its continuously sampled and temporarily stored in memory. Concurrent analysis of the data in memory during storage locates the pulse width at a prescribed percentage (e.g., 50%) of the peak amplitude of the pulse. This pulse width data is then processed to determine the pulse amplitude at the midpoint of the width of the pulse between its mid-peak values on rising edge and fall edge portions of the pulse.

While we have shown and described an embodiment in accordance with the present invention, it is to be understood that the same is not limited thereto but is susceptible to numerous changes and modifications as known to a person skilled in the art. For example, the data memory can be read out at a speed higher than the rate at which data is written into the memory (e.g., twice as fast, as a non-limiting example). Further, the invention may be employed in a multi-channel system having multiple and different types of sensors. Moreover, the invention may be incorporated for various types of measurements other than peak value, such as but not limited to correlation and fast Fourier transform processing systems. In addition, although the illustrated and described example references measurements of half-peak or a fifty percent value, the invention is applicable to other percentages of peak, such as but not limited to seventy-five percent of peak. We therefore do not wish to be limited to the details shown and described herein, but intend to cover all such changes and modifications as are obvious to one of ordinary skill in the art.

What is claimed:

1. In a flow cell measurement apparatus, a method of processing a pulse representative of a particle passing through a particle measurement aperture, comprising the steps of:
   (a) writing successive digitized samples of said pulse into memory and processing successive digitized samples of said pulse to determine a first and a second address in said memory, respectively, of a prescribed percentage of peak value on a rising edge of said pulse and said prescribed percentage of peak value on a falling edge of said pulse; and
   (b) processing the first address and the second address to locate one of said digitized samples in said memory to determine an amplitude of said pulse at a predetermined percentage of a distance between said prescribed percentage of peak value on said rising edge of said pulse and said prescribed percentage of peak value on said falling edge of said pulse.

2. The method according to claim 1, wherein step (a) comprises processing said successive digitized samples of said pulse to locate a half-peak value on a rising edge of said pulse and a half-peak value on a falling edge of said pulse, and step (b) comprises processing times of occurrence of said half-peak value on said rising edge of said pulse and said half-peak value on said falling edge of said pulse to determine the amplitude of said pulse at a point on said pulse midway between said half-peak value on said rising edge of said pulse and said half-peak value on said falling edge of said pulse.

3. The method according to claim 2, wherein step (a) comprises the steps of:
   (a1) selectively writing successive samples of said pulse into a peak register over the duration of said pulse, so as to store the peak of said pulse,
   (a2) for each sample of said pulse, incrementing a count within a pulse duration counter,
   (a3) processing said peak of said pulse as stored in step (a1) to locate the half-peak value on the rising edge of said pulse, and
   (a4) processing successive digitized samples of said pulse and said sampled half-peak value on the rising edge of said pulse to locate the half-peak value on the falling edge of said pulse.

4. The method according to claim 3, wherein step (b) comprises processing addresses of said memory that contains the half-peak value on the rising edge of said pulse and the half-peak value on the falling edge of said pulse, to determine the address in said memory containing the amplitude of said pulse at a point on said pulse midway between said half-peak value on said rising edge of said pulse and said half-peak value on said falling edge of said pulse.

5. The method according to claim 4, further including step (c) of providing as outputs: 1—the amplitude of said pulse at a point on said pulse midway between said half-peak value on said rising edge of said pulse and said half-peak value on said falling edge of said pulse; and 2—the width of said pulse between said half-peak value on said rising edge of said pulse and said half-peak value on said falling edge of said pulse.

6. A digital processing apparatus for use with a flow cell measurement system for processing a successive digitized samples of a pulse representative of a particle passing through a particle measurement aperture, comprising:
   data storage memory into which successively digitized samples of said pulse are written;
   a first digital processing circuit which is operative to process successive digitized samples of said pulse to determine a first and a second address in said memory, respectively, of a prescribed percentage of peak value on a rising edge of said pulse and said prescribed percentage of peak value on a falling edge of said pulse; and
   a second digital processing circuit which is operative to process the first address and the second address to locate one of said digitized samples in said memory to determine an amplitude of said pulse at a predetermined percentage of a distance between said prescribed percentage of peak value on said rising edge of said pulse and said prescribed percentage of peak value on said falling edge of said pulse.

7. The digital processing apparatus according to claim 6, wherein said first digital processing circuit is operative to process said successive digitized samples of said pulse to locate a half-peak value on a rising edge of said pulse and a half-peak value on a falling edge of said pulse, and said second digital processing circuit is operative to process times of occurrence of said half-peak value on said rising edge of said pulse and said half-peak value on said falling edge of said pulse to determine the amplitude of said pulse at a point on said pulse midway between said half-peak value on said rising edge of said pulse and said half-peak value on said falling edge of said pulse.

8. The digital processing apparatus according to claim 7, wherein said first digital processing circuit includes a peak value storage register into which successive samples of said pulse are selectively written over the duration of said pulse, so that at the conclusion of said pulse said peak value storage register contains a value corresponding to the peak amplitude of said pulse, and a pulse duration counter which is incremented by the pulse sampling clock so as to provide a count corresponding to the duration of said pulse, and wherein said second digital processing circuit is operative to process said peak of said pulse as stored in said peak value storage register to locate the half-peak value on the rising edge of said pulse, and to process successive digitized samples of said pulse and said sampled half-peak value on the rising edge of said pulse to locate the half-peak value on the falling edge of said pulse.

9. The digital processing apparatus according to claim 8, wherein said second digital processing circuit is operative to process addresses of said memory that contain the half-peak value on the rising edge of said pulse and the half-peak value on the falling edge of said pulse, to determine the address in said memory containing the amplitude of said pulse at a point on said pulse midway between said half-peak value on said rising edge of said pulse and said half-peak value on said falling edge of said pulse.

10. The digital processing apparatus according to claim 9, wherein said apparatus is operative to provide as outputs: 1—the amplitude of said pulse at a point on said pulse midway between said half-peak value on said rising edge of said pulse and said half-peak value on said falling edge of said pulse; and 2—the width of said pulse between said half-peak value on said rising edge of said pulse and said half-peak value on said falling edge of said pulse.

* * * * *